(12) United States Patent
Tom Dieck et al.

(10) Patent No.: US 9,017,707 B2
(45) Date of Patent: *Apr. 28, 2015

(54) COSMETIC OR DERMATOLOGICAL PREPARATIONS CONTAINING LICOCHALCONE A OR AN EXTRACT OF RADIX GLYCYRRHIZAE INFLATAE, CONTAINING LICOCHALCONE A

(71) Applicants: Karen Tom Dieck, Hamburg (DE); Ludger Kolbe, Dohren (DE); Claudia Mundt, Zurich (CH); Ursula Wensorra, Hamburg (DE); Rainer Wolber, Hamburg (DE)

(72) Inventors: Karen Tom Dieck, Hamburg (DE); Ludger Kolbe, Dohren (DE); Claudia Mundt, Zurich (CH); Ursula Wensorra, Hamburg (DE); Rainer Wolber, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/897,793

(22) Filed: May 20, 2013

(65) Prior Publication Data

US 2013/0253068 A1 Sep. 26, 2013

Related U.S. Application Data

(63) Continuation of application No. 10/889,114, filed on Jul. 13, 2004, now Pat. No. 8,470,349, which is a continuation of application No. PCT/EP03/05660, filed on May 30, 2003.

(30) Foreign Application Priority Data

Jun. 1, 2002 (DE) .................................. 102 24 387

(51) Int. Cl.
| | | |
|---|---|---|
| A61K 31/12 | (2006.01) | |
| A61K 8/97 | (2006.01) | |
| A61K 8/35 | (2006.01) | |
| A61Q 19/00 | (2006.01) | |
| A61K 8/86 | (2006.01) | |
| A61K 8/34 | (2006.01) | |

(52) U.S. Cl.
CPC .................. *A61K 31/12* (2013.01); *A61K 8/345* (2013.01); *A61K 8/35* (2013.01); *A61K 8/86* (2013.01); *A61K 8/97* (2013.01); *A61Q 19/00* (2013.01); *A61Q 19/004* (2013.01)

(58) Field of Classification Search
CPC ........... A61K 31/12; A61K 8/97; A61K 8/35; A61K 8/345; A61K 8/86; A61Q 19/00; A61Q 19/004
See application file for complete search history.

(56) References Cited

U.S. PATENT DOCUMENTS

| | | |
|---|---|---|
| 4,278,657 A * | 7/1981 | Tezuka et al. .................... 424/63 |
| 5,346,691 A | 9/1994 | Raspanti |
| 5,403,944 A | 4/1995 | Frater et al. |
| 5,609,875 A | 3/1997 | Hadas |
| 5,747,009 A | 5/1998 | Hansenne |
| 5,786,381 A | 7/1998 | Franklin et al. |
| 5,804,203 A | 9/1998 | Hahn et al. |
| 5,955,060 A | 9/1999 | Huglin et al. |
| 7,824,717 B2 | 11/2010 | Staeb et al. |
| 2001/0007677 A1 | 7/2001 | Nagatani et al. |
| 2002/0115622 A1 | 8/2002 | Kumagai et al. |
| 2005/0136139 A1 | 6/2005 | Kruse et al. |
| 2005/0158350 A1 | 7/2005 | Max et al. |
| 2005/0186295 A1 | 8/2005 | Stab et al. |
| 2005/0158259 A1 | 9/2005 | Albrecht et al. |
| 2005/0191266 A1 | 9/2005 | Raschke et al. |
| 2005/0201967 A1 | 9/2005 | Albrecht et al. |
| 2006/0292253 A1 | 12/2006 | Kruse et al. |
| 2007/0110704 A1 | 5/2007 | Gallinat et al. |
| 2007/0196289 A1 | 8/2007 | Blatt et al. |

FOREIGN PATENT DOCUMENTS

| | | |
|---|---|---|
| EP | 0570838 A1 | 11/1993 |
| EP | 775698 A1 | 5/1997 |
| EP | 0775698 A1 | 5/1997 |
| EP | 0998939 | 5/2000 |
| JP | 62181202 | 8/1987 |
| JP | 02204417 | 8/1990 |
| JP | 02204495 | 8/1990 |
| JP | 04297418 | 10/1992 |
| JP | 10077221 | 3/1998 |
| JP | 2000212060 | 8/2000 |
| JP | 2001163718 | 6/2001 |
| JP | 2002080343 | 3/2002 |
| WO | 9220690 A1 | 11/1992 |
| WO | 0215873 A1 | 2/2002 |

OTHER PUBLICATIONS

Frosch P.J., Kligman A.M. "A method for appraising the stinging capacity of topically applied substances", Journal of the Society of Cosmetic Chemists, 28, 197-209, May 1997.
Chemical Abstracts, vol. 123, 1995, 275242j.
Chemical Abstracts, vol. 111, 1989, 102481k.
http://biotechnologia.pl.
Remington's: The Science and Practice of Pharmacy, 19th Edition, vol. 1, p. 806.
Cohen, A.F. et al., J. A. Board. Fam. Pract. 2002, 15, pp. 214-217.
Millikan, L., Skinmed: Dermatology for the Clinican 2003, 2, pp. 43-47.
Shibata, S, et al., Planta Medica 1991, 57, pp. 221-224.
"Eucerin: Dermatologist-Preferred Skin Care", available at: http://www.eucerinus.com/products/face_err_dailylotion.html.
http://www.walgreens.com/store/product.jsp?CATID=100738&navAction=jump&navCount=1&id=prod1401814.
Kobayashi M. et al. "Antibacterial Activity of Licochalcone A against Spore-Forming Bacteria", Antimicrobial Agents and Chemotherapy, vol. 46, No. 5, May 2002, pp. 1226-1230.
Wenniger & McEwen, Jr., International Cosmetic Ingredient Dictionary and Handbook, pp. 301-307, 1997.

* cited by examiner

*Primary Examiner* — Renee Claytor
(74) *Attorney, Agent, or Firm* — Abel Law Group, LLP

(57) ABSTRACT

Disclosed are cosmetic or dermatological preparations for the treatment or alleviation of erythema which comprise an aqueous extract of Radix Glycyrrhizae inflatae or licochalcone A and optionally one or more ethoxylated or propoxylated raw materials and/or one or more polyols.

20 Claims, No Drawings

COSMETIC OR DERMATOLOGICAL PREPARATIONS CONTAINING LICOCHALCONE A OR AN EXTRACT OF RADIX GLYCYRRHIZAE INFLATAE, CONTAINING LICOCHALCONE A

CROSS-REFERENCE TO RELATED APPLICATIONS

The present application is a continuation of U.S. application Ser. No. 10/889,114, filed on Jul. 13, 2004, which is a continuation of International Application Number PCT/EP03/05660, filed on May 30, 2003; the disclosures of these applications are expressly incorporated by reference herein in their entireties.

BACKGROUND OF THE INVENTION

The present invention relates to active ingredients of cosmetic or dermatological preparations for the prophylaxis and treatment of inflamed skin conditions and/or skin protection in dry skin determined to be sensitive.

Furthermore the invention relates to the use of such active ingredients and preparations containing such active ingredients for the immunostimulation of the skin, thereby advantageously also for immunostimulation in terms of a treatment of injured skin, in particular for the treatment of wounds.

Moreover, the invention relates to preparations with extremely low so-called "stinging potential" and cosmetic or dermatological formulations that care for the skin—e.g., after sun-bathing—in a targeted manner and reduce the after reactions of the skin to the action of UV radiation.

The skin, in particular the epidermis, as the barrier organ of the human organism, is subjected to a particular extent to external influences. According to current scientific knowledge, the skin represents an immunological organ that as an immunocompetent peripheral compartment has its own role in inductive effective and regulative immunological processes of the organism in its entirety.

The epidermis is richly equipped with nerves and peripheroceptors such as lamellated corpuscles, Merkel cell neuritic complexes and free nerve endings for pain sensation, cold sensation, heat sensation and itching.

Immunosuppression in general is the suppression or reduction of the reactivity of the immune system. Immunosuppression can be divided into local and systemic effects. Ultimately it covers a plurality of different aspects that all include a reduction of the normal immunological defense mechanisms of the skin. It is known that ultraviolet (UV) light, as is contained in sunlight, can lead to immunosuppression. In the irradiation of the skin with UV light (in particular UVB light) both local and systemic aspects of UV-induced immunosuppression are observed (<Engl.> "to sting"=to injure, burn, be painful).

In people with delicate, sensitive or easily injured skin, a neurosensory phenomenon known as "stinging" can be observed. This "sensitive skin" is fundamentally different from "dry skin" with thickened and hardened horny layers of the epidermis.

Typical reactions of "stinging" with sensitive skin are reddening, tightening and burning of the skin, as well as itching.

"Stinging" phenomena can be considered disorders that are to be treated cosmetically. In contrast, severe itching, in particular with severe itchy skin occurring with atopy and itching with skin diseases, can also be labeled as a more serious dermatological disorder or a neurosensory phenomenon.

Typical disturbing neurosensory phenomena associated with the terms "stinging" or "sensitive skin" are reddening of the skin, tingling, prickling sensation, tightening and burning of the skin and itching. They can be caused by stimulating environmental conditions, e.g., massage, effect of (detergent) surfactants, weather influence, such as sun, cold, dryness, as well as humid heat, thermal radiation and UV radiation, e.g., by the sun.

In the *Journal of the Society of Cosmetic Chemists*, 28, p. 197-209 (May 1977) P. J. Frosch and A. M. Kligman describe a method of estimating the "stinging potential" of topically applied substances. As positive substances, e.g., lactic acid and pyruvic acid are used here. In measuring according to this method, however, amino acids, in particular glycine, were also determined to be neurosensorily active (such substances are called "stingers").

According to previous findings, such a sensitivity to particular substances occurs differently from individual to individual. This means that a person who experiences a "stinging effect" on contact with a substance, will in all probability experience it again on each further contact. However, contact with other "stingers" is just as likely to occur without any reaction.

Many more or less sensitive people also suffer from erythematous skin conditions at the use of some deodorizing or antiperspirant preparations.

Furthermore, erythematous skin conditions also occur as concomitant symptoms with certain skin diseases or irregularities. For example, the typical rash in the external manifestation of acne is regularly more or less severely reddened.

In people sensitive thereto, also shaving induces erythema, burning, itching and tightening that are caused by the superficial injury and the mechanical stress of the upper dermal layers with both wet shaving and dry shaving. These symptoms often occur with the daily shaving of the beard, but irritation can also occur after shaving armpits, bikini line and legs.

In addition to the positive effects of sunlight, such as general well-being, the formation of vitamin D3 and acne treatment, there are also negative effects that should be combated.

The conditions of sunbathing represent an unaccustomed—in part extreme—strain on the human organism by which the skin in particular is affected. As long as the radiation stress does not exceed a certain level, our skin can cope with it. Slighter damage, as is present in imperceptible sub-erythema, is repaired immediately. However, if the skin is exposed for too long to the sun or an artificial source of radiation, after a latency period of 2 to 3 hours a reddening of the skin that is very distinguishable from the non-irradiated skin develops, the erythema solare. With the sunburn that thus occurs a distinction is made between $1^{st}$ degree: erythema (reddening, feeling of warmth, burning, tightening of the skin) subsides again after 2 to 3 days and disappears with simultaneously increasing pigmentation, $2^{nd}$ degree: blistering
  blisters form on the skin with burning and itching, the epidermis is sloughed extensively $3^{rd}$ degree: cell damage
  deep cell damage occurs, the body reacts with raised temperature, the epidermis is sloughed very extensively.

The $2^{nd}$ and $3^{rd}$ degrees are also called solar dermatitis.

The formation of the erythema depends on the wavelength. The erythema range of UV B is between 280 nm and 320 nm.

Approximately 90% of the ultraviolet radiation reaching the earth is made up of UV A rays with a wavelength of between 320 nm and 400 nm. Whereas the UV B radiation varies greatly depending on numerous factors (e.g., time of the year and time of the day or degree of latitude), the UV A radiation remains relatively constant day by day regardless of the time of year or the time of day or geographical factors. At the same time most of the UV A radiation penetrates the living epidermis, whereas about 70% of the UV B radiation is stopped by the horny layer of the epidermis.

For a long time it was mistakenly assumed that the long-wavelength UV A radiation has only a negligible biological effect and that accordingly the UV B rays are responsible for most light damage to the human skin. However, in the meantime it has been proven by numerous studies that UV A radiation is much more dangerous than UV B radiation in terms of triggering photodynamic, specifically phototoxic reactions and chronic changes to the skin. The damaging effect of UV B radiation can also be further increased by UV A radiation.

Since the contributions of the various wavelength ranges of UV light to changes in the skin caused by light have not been fully determined, today it is increasingly assumed that preventive protection against both UV A and UV B rays, e.g., through the application of sunscreen filter substances in the form of a cosmetic or dermatological formulation on the skin, is of fundamental importance. Cosmetic or dermatological means, applied to the skin in a thin layer, are to protect the skin from the negative effects of solar radiation.

Most people find sunbathing pleasant and at first do not consider the disadvantageous effects. However, in recent years an awareness has certainly developed about the negative effects of too intensive an exposure to sunlight, which is why more sunscreens and sunscreens with greater protection are being used.

Sunburn or photo-erythema are the acute manifestations of the effect of light. In addition to the effects of UV rays already described, in the after reaction of the skin a reduced production of sebum and a drying of the skin also occur. So-called after-sun preparations are used to treat the skin, the application of which is on principle recommended after each exposure to the sun. These are as a rule emulsions or aqueous hydrogels that in addition to conventional moisturizing substances can also contain special active ingredients, such as, e.g.:

anti-inflammatory and cooling substances,
  locally anesthetizing substances and/or
  disinfecting substances in order to prevent possible skin infections.

Anti-inflammatory active ingredients extracted, e.g., from plants, such as azulene and bisabolol (chamomile), glycyrrhizin (licorice root), hamamelin (witch hazel) or whole extracts, e.g., from aloe vera or chamomile are used. With lighter forms and locally limited erythema reactions, these show some success. The same applies to creams with a high content of essential oils or panthenol.

After sun preparations are intended to cool the skin after sunbathing and to improve its humectant capacity, whereby conveying the cooling effect has a central role. This cooling effect is achieved, e.g., by high quantities of ethanol that evaporates spontaneously on the application of the formulation to the skin. As a result of the cold due to evaporation of the aqueous phase, hydrogels, o/w emulsions (lotions) or aqueous lotions also have a pronounced cooling effect that leads to an alleviation of the inflammation through a local vasoconstriction.

The object of the present invention was to overcome the disadvantages of the prior art and to provide active ingredients and preparations containing such active ingredients for the cosmetic and dermatological treatment and/or prophylaxis of erythematous, inflammatory, allergic or auto-immune reactive symptoms, in particular dermatoses, but also of the manifestation of "stinging."

Furthermore, such active ingredients or preparations containing such active ingredients were to be provided which can be used for the immunostimulation of the skin, thereby also advantageously for immunostimulation in the sense of the effect of promoting wound healing.

The term "inflammation" is a relatively extensive and old term. Even before Christ, Aulus Celsus introduced four of the five cardinal signs of inflammation: rubor, tumor, calor and dolor (reddening, swelling, heat and pain). In the second century Galen of Pergamon defined the fifth sign: functio laesa (restricted function). In all, inflammation research has been going on for 2000 years, 200 years of them at cellular level and 20 years at molecular level. It has thereby become more and more obvious that the term is nonuniform.

Inflammatory disorders are characterized by infiltrates of inflammatory cells, which, however, can be composed very differently. Psoriasis, an inflammatory skin disorder, is, e.g., characterized by an infiltrate of oligoclonal T cells and polymorphonuclear granulocytes in sharply defined inflammatory plaques. The involved skin of the atopic eczema, however, is characterized by infiltrating T cells against environmental antigens and eosinophilic granulocytes. The therapies with anti-inflammatory substances are equally as diverse as the inflammatory manifestations.

It cannot by any means be assumed that a substance that shows a very good effect with one inflammatory disorder will also have the same effect with other inflammations. Intensive research is therefore being conducted in this field, many of these usually chronic disorders are still impossible to treat satisfactorily. Adrenocortical steroids come closest to such an all-embracing effect, but because of the in part serious side-effects they cannot be considered for a continuous and lengthy application. Adrenocortical steroids are even completely banned for cosmetic applications for this reason, other substances have to be used here.

Cosmetics for soothing the skin are used with acute skin irritations; these are to be distinguished from the (chronic) inflammations described above. The cause of irritations can be, e.g., physical stimuli such as UV radiation or shaving. In particular in the early stage and with a slight degree of stimulus, there is no infiltrate of inflammatory cells (T cells, macrophages, granulocytes, . . . ), instead the affected skin cells (mainly keratinocytes and fibroblasts) themselves produce an abundance of pro-inflammatory mediators. These mediators activate the cells, induce defense and repair mechanisms and subsequently attract inflammatory cells. The object of the soothing effect on the skin of cosmetics must therefore be to prevent the negative consequences of the irritation, without blocking the necessary repair mechanisms. The known anti-inflammatory substances that are to act above all on the infiltrating cells can therefore only be used to a limited extent as model substances.

It was surprising and therein lies the solution to these objects, that the use of licochalcone A or in cosmetic preparations for the care and/or alleviation of erythema caused by physical irritation of the skin would overcome the disadvantages of the prior art.

A use according to the invention is particularly advantageous, characterized in that the preparations contain 0.0001 to 5% by weight, in particular 0.001 to 1% by weight, very particularly 0.005 to 0.15% by weight licochalcone A with respect to the total weight of the preparation.

Furthermore, a use according to the invention is particularly advantageous, characterized in that the preparations contain 0.001 to 10% by weight, in particular 0.05 to 5% by weight, very particularly 0.01 to 2% by weight of one or more ethoxylated or propoxylated raw materials, with respect to the total weight of the preparation.

Furthermore, a use according to the invention is particularly advantageous, characterized in that the preparations contain 0.001 to 10% by weight, in particular 0.05 to 5% by weight, very particularly 0.01 to 2% by weight of one or more polyols with respect to the total weight of the preparation.

Furthermore, a use according to the invention is particularly advantageous characterized in that the preparations contain licochalcone as a constituent of plant extracts, in particular radix *glycyrrhizae inflatae*.

The preparations according to the invention are in every respect very satisfactory preparations that are characterized by an excellent effect. When using the active ingredients used according to the invention or cosmetic or topical dermatological preparations with an effective content of active ingredients used according to the invention an effective treatment is possible as well as a prophylaxis of inflammatory skin conditions—including atopic eczema—and/or for skin protection with dry skin determined to be sensitive. However, the active ingredient according to the invention or cosmetic or topical dermatological preparations with an effective content of an active ingredient according to the invention surprisingly also serves to soothe sensitive or irritated skin.

It was not foreseeable to one of skill in the art that the preparations according to the invention
 better care for light-stressed skin or
 skin stressed from shaving,
 better reduce the after reactions of the skin to the effect of UV radiation,
 better soothe skin irritated from sunbathing,
 would cause slight sunburn to subside more quickly,
 act better than moisturizing preparations,
 are easier to formulate
 better promote the smoothing of the skin and
 would be characterized by better care effect
than the preparations of the prior art.

Naturally the invention is not restricted to preparations that are used after sunbathing; it also naturally encompasses all cosmetic and dermatological applications in which an anti-inflammatory effect is desirable or could be advantageous.

Here razor burn should be mentioned in particular, as often occurs after shaving.

The subject matter of the invention is therefore furthermore the use of cosmetic or dermatological formulations with a content of
 an aqueous extract of radix glycyrrhizae inflatae
 one or more ethoxylated or propoxylated raw materials
 optionally one or more polyols,
within the scope of the present disclosure also collectively called "combination of active ingredients according to the invention" for the care of skin stressed by light and shaving and/or to alleviate the after reactions of the skin to the effect of UV radiation and/or shaving.

The plant species *glycyrrhiza inflata* like the medicinal liquorice *glycyrrhiza glabra* in Europe belongs to the glycyrrhiza genus that belongs to the fabaceae plant family (legumes). The drug radix *glycyrrhizae inflatae*, i.e., the root of the plant, is conventional, e.g., in Far Eastern medicine. The use of the drug as an anti-inflammatory agent is likewise known.

One constituent of the aqueous extract of radix glycyrrhizae inflatae is licochalcone A, which is characterized by the following structural formula:

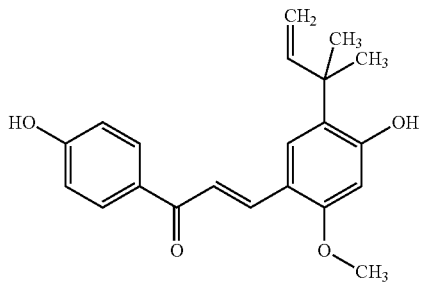 [SMILES: C=CC(C)(C)c1cc(/C=C/C(=O)c2ccc(O)cc2)c(OC)cc1O]

It is assumed that this substance, possibly in synergy with the other constituents of the extracts, has a part in the effect according to the invention.

Therefore cosmetic or dermatological preparations with a content of
 licochalcone A
 water
 one or more ethoxylated or propoxylated raw materials
 if necessary one or more polyols
are also according to the invention.

It is advantageous according to the invention if the cosmetic or dermatological preparations contain 0.001 to 10% by weight, in particular 0.05 to 5% by weight, very particularly 0.01 to 2% by weight of an aqueous extract of radix glycyrrhizae inflatae with respect to the total weight of the preparation.

It is advantageous according to the invention if the cosmetic or dermatological preparations contain 0.001 to 10% by weight, in particular 0.05 to 5% by weight, very particularly 0.01 to 2% by weight of one or more ethoxylated or propoxylated raw materials with respect to the total weight of the preparation.

In particular it is advantageous to select PPG-6-decyltetradeceth-30 as ethoxylated or propoxylated raw materials.

According to the invention it is advantageous if the cosmetic or dermatological preparations contain 0.001 to 10% by weight, in particular 0.05 to 5% by weight, very particularly 0.01 to 2% by weight of one or more polyols with respect to the total weight of the preparation.

In particular it is advantageous to select butylene glycol as the polyol.

It is very particularly advantageous to start from an aqueous extract that can be obtained under the name Aqua Licorice Extract P-U from Maruzen, which is an aqueous mixture (approx. 10% by weight water) of radix *glycyrrhizae inflatae* (approx. 5% by weight, proportion of licochalcone A in the extract approx. 22%, PPG-6-decyltetradeceth-30 (approx. 25% by weight) and butylene glycol (approx. 60% by weight).

Furthermore it is advantageous to use licochalcone A in other vehicle systems in a concentration of 0.0001 to 5% by weight, in particular 0.001 to 1% by weight, very particularly 0.005-0.05% by weight.

Within the scope of the present invention it is preferred if the cosmetic or dermatological preparations according to the invention contain one or more alcohols, in particular if the formulations are present in the form of an after sun preparation and are intended to be characterized by a particular cooling effect.

The cosmetic or dermatological formulations according to the present invention can preferably contain in addition to one or more oil phases one or more aqueous phases and can be present, e.g., in the form of W/O, O/W, W/O/W or O/W/O emulsions. Such emulsions can preferably also be a microemulsion, a Pickering emulsion or a sprayable emulsion.

Preferably, the formulations according to the invention also contain further anti-inflammatory substances, such as, e.g., allantoin, α-bisabolol, pantothenic acid, panthenol, royal jelly, chamomile extract, azulene or aloe vera extract and unsaponifiable constituents of avocado or soybean oil and further substances that soothe irritated skin. Further advantageous active ingredients are tannins, which have an astringent, anti-inflammatory and or secreto-inhibitory effect.

Moreover, the formulations according to the invention can also advantageously contain dihydroxyacetone or nut extracts as well as other substances intended to maintain a tan.

The cosmetic or dermatological formulations according to the invention can have the usual composition and can be used in particular to treat and care for the skin and/or the hair after sunbathing and as a make-up product in decorative cosmetics. Accordingly the formulations according to the invention—depending on their structure—can be used, e.g., as skin protection cream, cleansing milk, sun screen lotion, nutrient cream, day or night cream, etc. Optionally, it is possible and advantageous to use the formulations according to the invention as the basis for pharmaceutical formulations. In particular those cosmetic and dermatological formulations are preferred that are present in the form of an after sun skin care product or an after shave product.

For use, the cosmetic and dermatological preparations according to the invention are applied in the manner usual for cosmetics, i.e., e.g., directly on the skin and/or the hair in sufficient amounts after removal from a bottle, tube, pot or other container, or with the aid of an (impregnated) cloth.

As objects of daily use, impregnated cloths find wide application in various fields. Among other things, they permit efficient cleansing and care gentle to the skin even in the absence of (running) water. The actual utensil thereby comprises two components:
 a) a dry cloth that is made of materials such as paper and/or a large variety of mixtures of natural or artificial fibers and
 b) a low-viscosity impregnation solution.

Cosmetic and dermatological cloths that are moistened with cosmetic or dermatological impregnation solutions that have a content of a combination of active ingredients according to the invention are therefore also an object of the present invention.

"Dry" cloths (according to a)) preferred according to the invention are made of a nonwoven fabric, in particular water jet-reinforced and/or water-jet-embossed nonwoven fabric.

Such nonwoven fabrics can have macroembossing of any desired pattern. The selection to be made is guided on the one hand by the impregnation to be applied and on the other hand by the use to which the later cloth is to be put.

It has proven to be advantageous for the cloth if it has a weight of 35 to 120 g/m$^2$, preferably 40 to 60 g/m$^2$ (measured at 20° C.±2° C. and at a humidity of the ambient air of 65%±5% for 24 hours).

The thickness of the nonwoven fabric is preferably 0.4 mm to 2 mm, in particular 0.6 mm to 0.9 mm.

Generally all organic and inorganic fibrous materials on a natural and synthetic basis can be used as starting materials for the nonwoven fabric of the cloth. By way of example there may be listed viscose, cotton, cellulose, jute, hemp, sisal, silk, wool, polypropylene, polyesters, polyethylene terephthalate (PET), aramid, nylon, polyvinyl derivatives, polyurethanes, polylactide, polyhydroxyalkanoate, cellulose esters and/or polyethylene and also mineral fibers such as glass fibers or carbon fibers. However, the present invention is not limited to the cited materials; a plurality of other fibers can be used to form the nonwoven fabric. Within the scope of the present invention it is particularly advantageous if the fibers used are not water-soluble.

In a particularly advantageous embodiment of the nonwoven fabric, the fibers are made of a mixture of 70% viscose and 30% PET.

Fibers of high-strength polymers, such as polyamide, polyester and/or ultrastretched polyethylene are also particularly advantageous.

Moreover, the fibers can also be dyed to be able to emphasize and/or increase the visual attractiveness of the nonwoven fabric. In addition the fibers can contain UV stabilizers and/or preservatives.

The fibers used to form the cloth preferably have a water absorption rate of more than 60 mm/[10 min] (measured by the EDANA Test 10.1-72), in particular more than 80 mm/[10 min].

Furthermore, the fibers used to form the cloth preferably have a water absorption capacity of more than 5 g/g (measured by the EDANA Test 10.1-72), in particular more than 8 g/g.

Within the scope of the present invention it is advantageous if the weight ratio of the unimpregnated cloth to the impregnation solution is selected from the range of from 2:1 to 1:6.

The cosmetic and dermatological formulations or preparations cited within the scope of the description of the present invention represent advantageous impregnation solutions for cosmetic and dermatological cloths within the scope of the present invention.

It is advantageous if the impregnation solutions according to the invention are highly fluid, in particular sprayable and have, e.g., a viscosity of less than 2,000 mPa s, in particular less than 1,500 mPa s (measuring apparatus: Haake Viskotester VT-02 at 25° C.).

The cosmetic and dermatological formulations according to the invention can contain cosmetic auxiliary agents as are normally used in such preparations, e.g., preservatives, bactericides, perfumes, substances to prevent foaming, dyes, pigments that have a coloring effect, thickening agents, moistening and/or moisture-containing substances, fats, oils, waxes or other normal components of a cosmetic or dermatological formulation, such as alcohols, polyols, polymers, foam stabilizers, electrolytes, organic solvents and/or silicone derivatives and moisturizers.

Substances or substance mixtures are termed moisturizers which endow cosmetic or dermatological preparations with the property of reducing the loss of moisture of the horny layer of the epidermis (also called trans-epidermal water loss (TEWL)) and/or positively influencing the hydration of the horny layer of the epidermis after application or distribution on the skin surface.

Within the scope of the present invention, advantageous moisturizers are, e.g., glycerin, lactic acid, pyrrolidone carboxylic acid and urea. Furthermore, it is particularly advantageous to use polymer moisturizers from the group of polysaccharides that are water-soluble and/or can be swelled in water and/or can be gelled with the aid of water. Particularly advantageous, for example, are hyaluronic acid and/or a fucose-rich polysaccharide which is filed in the Chemical Abstracts under registration number 178463-23-5 and can be obtained, e.g., under the designation Fucogel®1000 from SOLABIA S.A.

Glycerin can be used as moisturizer within the scope of the present invention in the range of 0.05-30% by weight, particularly preferably 1-10%.

The amounts of cosmetic or dermatological auxiliary agents and carriers and perfume to be used in each case can be easily determined by simple testing by one of skill in the art depending on the type of the respective product.

An additional amount of antioxidants is generally preferred. According to the invention, all antioxidants suitable or usual for cosmetic and/or dermatological applications can be used as favorable antioxidants.

The antioxidants are advantageously selected from the group consisting of amino acids (e.g. glycine, histidine, tyrosine, tryptophan) and their derivatives, imidazoles (e.g. urocanic acid) and their derivatives, peptides such as D,L-carnosine, D-carnosine, L-carnosine and their derivatives (e.g. anserine), carotinoids, carotenes (e.g., α-carotene, β-carotene, lycopene) and their derivatives, lipoic acid and its derivatives (e.g. dihydrolipoic acid), aurothioglucose, propylthiouracil and other thiols (e.g., thioredoxin, glutathione, cysteine, cystine, cystamine and their glycosyl-, N-acetyl-, methyl-, ethyl-, propyl-, amyl-, butyl- and lauryl-, palmitoyl-, oleyl-, γ-linoleyl-, cholesteryl- and glyceryl esters) and their salts, dilauryl thiodipropionate, distearyl thiodipropionate, thiodipropionic acid and their derivatives (esters, ethers, peptides, lipids, nucleotides, nucleosides and salts) as well as sulfoximine compounds (e.g. buthionine sulfoximines, homocysteine sulfoximine, buthionine sulfones, penta-, hexa-, heptathionine sulfoximine) in very low, well tolerated doses (e.g. pmol to μmol/kg), furthermore (metal) chelators (e.g., α-hydroxy fatty acids, palmitic acid, phytic acid, lactoferrin), α-hydroxy acids (e.g. citric acid, lactic acid, malic acid), humic acid, melanins, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, alanine diacetic acid, flavonoids, polyphenols, catechins, vitamin C and derivatives (e.g., ascorbyl palmitate, Mg ascorbyl phosphate, ascorbyl acetate), tocopherols and derivatives (e.g., vitamin E acetate), and coniferyl benzoate of benzoic resin, rutinic acid and its derivatives, ferulic acid and its derivatives, butylated hydroxytoluene, butylated hydroxyanisole, nordihydroguaiak resin acid, nordihydroguaiaretic acid, trihydroxybutyrophenone, uric acid and their derivatives, mannose and its derivatives, zinc and its derivatives (e.g. ZnO, ZnSO$_4$), selenium and its derivatives (e.g. selenium methionine), stilbenes and their derivatives (e.g. stilbene oxide, trans-stilbene oxide) and the derivatives of these named active substances suitable according to the invention (salts, esters, ethers, sugars, nucleotides, nucleosides, peptides and lipids).

The amount of the aforementioned antioxidants (one or more compounds) in the emulsions is preferably 0.001 to 30% by weight, particularly preferably 0.05 to 20% by weight, in particular 0.1 to 10% by weight with respect to the total weight of the preparation.

If vitamin E and/or its derivatives represent the antioxidant(s), it is advantageous to select its respective concentrations from the range of from 0.001 to 10% by weight, with respect to the total weight of the formulation.

If vitamin A or vitamin A derivatives or carotenes or their derivatives represent the antioxidant(s), it is advantageous to select their respective concentrations from the range of 0.001 to 10% by weight with respect to the total weight of the formulation.

The lipid phase can be advantageously selected from the following substance group:

mineral oils, mineral waxes oils, such as triglycerides of capric or caprylic acid, furthermore natural oils such as, e.g., castor oil;

fats, waxes and other natural and synthetic fat substances, preferably esters of fatty acids with alcohols with a low C number, e.g., with isopropanol, propylene glycol or glycerin, or esters of fatty alcohols with alkanoic acids with a low C number or with fatty acids;

alkyl benzoates;

silicon oils such as dimethylpolysiloxane, diethylpolysiloxane, diphenylpolysiloxane and mixed forms thereof.

The oil phase of the emulsions, oleogels or hydrodispersions or lipodispersions within the scope of the present invention is advantageously chosen from the group of esters of saturated and/or unsaturated, branched and/or unbranched alkane carboxylic acids of a chain length of 3 to 30 C atoms and saturated and/or unsaturated, branched and/or unbranched alcohols of a chain length of 3 to 30 C atoms, from the group of esters of aromatic carboxylic acids and saturated and/or unsaturated, branched and/or unbranched alcohols of a chain length of 3 to 30 C atoms. Such ester oils can then be advantageously chosen from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethyl hexyl palmitate, 2-ethyl hexyl laurate, 2-hexyl decyl stearate, 2-octyl dodecyl palmitate, oleyl oleate, oleyl erucate, erucyl oleate, erucyl erucate as well as synthetic, semi-synthetic and natural mixtures of such esters, e.g. jojoba oil.

Furthermore, the oil phase can be advantageously chosen from the group of branched and unbranched hydrocarbons and hydrocarbon waxes, silicone oils, dialkyl ethers, the group of saturated or unsaturated, branched or unbranched alcohols, as well as the fatty acid triglycerides, namely the triglycerine esters of saturated and/or unsaturated, branched and/or unbranched alkane carboxylic acids of a chain length of 8 to 24, in particular 12 to 18 C atoms. The fatty acid triglycerides can, for example, be advantageously chosen from the group of synthetic, semi-synthetic and natural oils, e.g. olive oil, sunflower oil, soybean oil, peanut oil, rape seed oil, almond oil, palm oil, coconut oil, palm nut oil and the like.

Also, any mixtures of such oil and wax components can be advantageously used in accordance with the present invention. It may optionally, also be advantageous to use waxes, for example cetyl palmitate, as sole lipid component of the oil phase.

The oil phase is advantageously selected from the group 2-ethylhexyl isostearate, octyl dodecanol, isotridecyl isononanoate, isoeicosane, 2-ethylhexyl cocoate, $C_{12-15}$-alkyl benzoate, capryl-capric acid triglyceride, dicaprylyl ether.

Mixtures of $C_{12-15}$-alkyl benzoate, and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous.

Of the hydrocarbons, paraffin oil, squalane and squalene can be advantageously used in accordance with the present invention.

The oil phase can, furthermore, advantageously have a content of cyclic or linear silicone oils or completely consist of such oils, it being preferable however, apart from the silicone oil or the silicone oils, to use an additional content of other oil phase components.

Cyclomethicone (octamethylcyclotetrasiloxane) is advantageously utilized as the silicone oil to be used according to the invention. However, other silicone oils can also be advantageously used in accordance with the invention, for example, hexamethyl cyclotrisiloxane, polydimethyl siloxane, poly(methylphenyl siloxane).

Furthermore, particularly advantageous are mixtures of cyclomethicone and isotridecyl isononanoate, of cyclomethicone and 2-ethylhexyl isostearate.

The aqueous phase of the formulations according to the invention optionally advantageously contains alcohols, diols or polyols of low C-number, as well as their ethers, preferably ethanol, isopropanol, propylene glycol, glycerin, ethylene glycol, ethylene glycol monoethyl- or -monobutyl ethers, propylene glycol monomethyl, -monoethyl or -monobutyl ethers, diethylene glycol monomethyl- or -monoethyl ethers and analogous products, also alcohols of low C-number, e.g., ethanol, isopropanol, 1,2-propane diol, glycerin and in particular one or more thickening agents, which can advantageously be chosen from the group: silicon dioxide, aluminum silicates, polysaccharides and/or their derivatives, e.g. xanthan gum and/or hydroxypropylmethyl cellulose, in each case individually or in combination.

It is also advantageous according to the present invention to produce cosmetic and dermatological preparations, the main purpose of which is not protection from sunlight, but which nevertheless have a content of UV protection substances. Thus, usually UV A or UV B filter substances are incorporated, e.g., in day creams or makeup products. In addition, UV protection substances, just like antioxidants and—if desired—preservatives represent an effective protection of the preparations themselves from spoiling. Furthermore, cosmetic and dermatological preparations are favorable that are present in the form of a sunscreen.

Accordingly, the preparations according to the present invention preferably contain in addition to the active ingredient according to the invention in addition at least one further UV A or UV B filter substance. Although not necessary, the formulations can optionally also contain one or more organic or inorganic pigments as UV filter substances, which can be present in the water and/or the oil phase.

Preferred inorganic pigments are metal oxides and/or other metal compounds difficult to dissolve in water or insoluble in water, in particular oxides of titanium ($TiO_2$), zinc (ZnO), iron (e.g., $Fe_2O_3$), zirconium ($ZrO_2$), silicon ($SiO_2$), manganese (e.g., MnO), aluminum ($Al_2O_3$), cerium ($Ce_2O_3$), mixed oxides of the corresponding metals and mixtures of such oxides.

Within the scope of the present invention, such pigments can be advantageously surface treated (coated), whereby, e.g., an amphiphilic or hydrophobic character is to be formed or retained. This surface treatment can consist in that the pigments are provided with a thin hydrophobic layer according to methods known per se.

According to the invention, titanium dioxide pigments coated with octylsilanol are, for example, advantageous. Suitable titanium dioxide particles can be obtained under the trade name T805 from Degussa. Also particularly advantageous are $TiO_2$ pigments coated with aluminum stearate, e.g. available under the trade name MT 100 T from TAYCA.

A further advantageous coating of the inorganic pigments consists of dimethylpolysiloxane (also: dimethicone), a mixture of completely methylated, linear siloxane polymers which are terminally blocked with trimethylsiloxy units. Particularly advantageous for the purposes of the present invention are zinc oxide pigments coated in this way.

Also advantageous is a coating of the inorganic pigments with a mixture of dimethylpolysiloxane, in particular dimethylpolysiloxane with an average chain length of from 200 to 350 dimethylsiloxane units, and silica gel, which is also referred to as simethicone. It is particularly advantageous if the inorganic pigments are additionally coated with aluminum hydroxide or aluminum oxide hydrate (also: alumina, CAS No.: 1333-84-2). Titanium dioxides which have been coated with simethicone and alumina are particularly advantageous, it being possible for the coating to also contain water. One example thereof is the titanium dioxide that can be obtained under the trade name Eusolex T2000 from Merck.

An advantageous organic pigment for the purposes of the present invention is 2,2'-methylenebis(6-(2H-benzotriazol-2-yl)-4-(1,1,3,3-tetramethylbutyl)phenol) [INCI: Bis-octyltriazole], which is available under the trade name Tinosorb® M from CIBA-Chemikalien GmbH.

Preparations according to the invention advantageously contain substances which absorb UV radiation in the UV-A and/or UV-B range, where the total amount of filter substances is, e.g., 0.1% by weight to 30% by weight, preferably 0.5 to 20% by weight, in particular 1.0 to 15.0% by weight, based on the total weight of the preparations, in order to make available cosmetic preparations which protect the hair or the skin from the entire range of ultraviolet radiation. They can also be used as sunscreen compositions for the hair or the skin.

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the trade mark Parsol® 1789 and by Merck under the trade name Eusolex® 9020.

Further advantageous UV-A filter substances are phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic acid bis-sodium salt having the INCI name Bisimadazylate, which is available, for example, under the trade name Neo Heliopan AP from Haarmann & Reimer.

Also advantageous are 1,4-di(2-oxo-10-sulfo-3-bornylidenemethyl)benzene and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid).

Advantageous UV filter substances for the purposes of the present invention are also so-called broadspectrum filters, i.e., filter substances which absorb both UV-A and UV-B radiation.

Advantageous broadspectrum filters or UV-B filter substances are, for example, bis-resorcinyltriazine derivatives. Particularly preferred are 2,4-bis{[4-(2-ethylhexyloxy)-2-hydroxy]phenyl}-6-(4-methoxyphenyl)-1,3,5-triazine (INCI: Aniso Triazine), which is available under the trade name Tinosorb® S from CIBA-Chemikalien GmbH.

Particularly advantageous preparations within the scope of the present invention, which are characterized by a high or very high UV-A protection, preferably contain several UV-A and/or broadspectrum filters, in particular dibenzoylmethane derivatives [for example 4-(tert-butyl)-4'-methoxydibenzoylmethane], benzotriazole derivatives [for example 2,2'-methylenebis(6-(2H-benzotriazol-2-yl)-4-(1,1,3,3-tetramethylbutyl)-phenol)], phenylene-1,4-bis(2-benzimidazyl)-3,3'-5, 5'-tetrasulfonic acid and/or its salts, 1,4-di(2-oxo-10-sulfo-3-bornylidenemethyl)benzene and/or salts thereof and/or 2,4-bis {[4-(2-ethyl-hexyloxy)-2-hydroxy]phenyl}-6-(4-methoxyphenyl)-1,3,5-triazine, in each case individually or in any combinations with one another.

Also other UV substances that have the structural formula

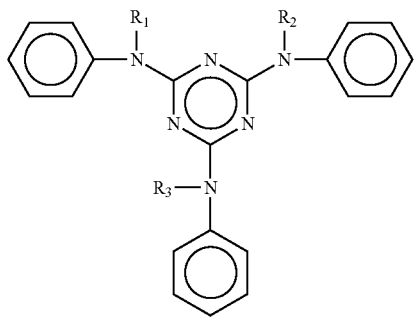

are advantageous UV filter substances within the scope of the present invention, for example the s-triazine derivatives described in European published patent application EP 570 838 A1, the chemical structure of which is given by the generic formula

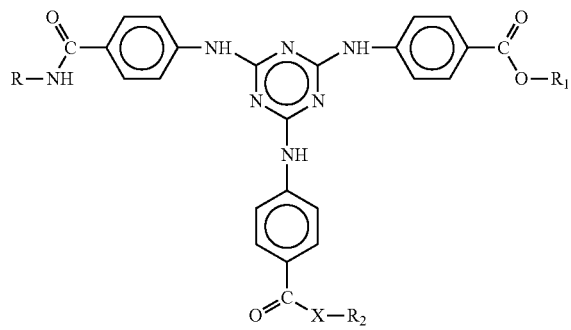

where
R is a branched or unbranched $C_1$-$C_{18}$-alkyl radical, a $C_5$-$C_{12}$-cycloalkyl radical, optionally substituted by one or more $C_1$-$C_4$-alkyl groups,
X is an oxygen atom or an NH group,
$R_1$ is a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

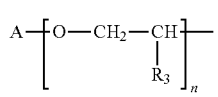

in which
A is a branched or unbranched $C_1$-$C_{18}$-alkyl radical, a $C_5$-$C_{12}$-cycloalkyl or aryl radical, optionally substituted by one or more $C_1$-$C_4$-alkyl groups,
$R_3$ is a hydrogen atom or a methyl group,
n is a number of from 1 to 10,
$R_2$ is a branched or unbranched $C_1$-$C_{18}$-alkyl radical, a $C_5$-$C_{12}$-cycloalkyl radical, optionally substituted by one or more $C_1$-$C_4$-alkyl groups, if X is the NH group, and a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

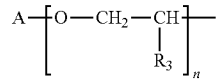

in which
A is a branched or unbranched $C_1$-$C_{18}$-alkyl radical, a $C_5$-$C_{12}$-cycloalkyl radical or aryl radical, optionally substituted by one or more $C_1$-$C_4$-alkyl groups,
$R_3$ is a hydrogen atom or a methyl group,
n is a number from 1 to 10,
if X is an oxygen atom.

A particularly preferred UV filter substance within the scope of the present invention is also an asymmetrically substituted s-triazine, the chemical structure of which is given by the formula

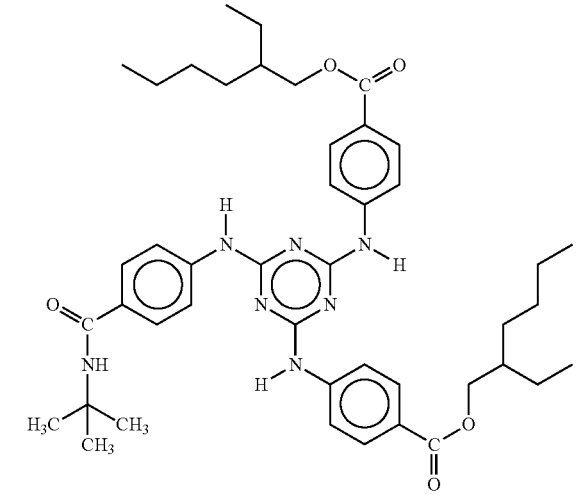

which is also referred to below as dioctylbutylamidotriazone (INCI: Dioctylbutamidotriazone) and is available under the trade name UVASORB HEB from Sigma 3V.

Also advantageous within the scope of the present invention is a symmetrically substituted s-triazine, tris(2-ethylhexyl) 4,4',4''-(1,3,5-triazine-2,4,6-triyltriimino)trisbenzoate, synonym: 2,4,6-tris [anilino(p-carbo-2'-ethyl-1$^1$-hexyloxy)]-1,3,5-triazine (INCI: Octyl Triazone), which is sold by BASF Aktiengesellschaft under the trade name UVINUL® T 150.

European published patent application 775 698 also describes preferably employable bis-resorcinyltriazine derivatives, the chemical structure of which is given by the generic formula

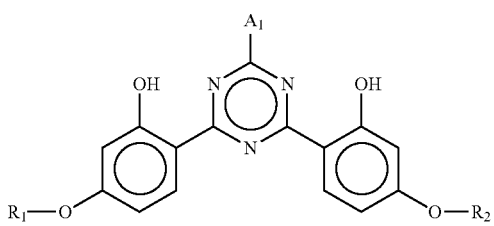

where $R_1$, $R_2$ and $A_1$ represent a large variety of organic radicals.

Also advantageous within the scope of the present invention are 2,4-bis{[4-(3-sulfonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}[4-(2-methoxyethyl-carboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis{[4-(2-ethyl-hexyloxy)-2-hydroxy]phenyl}-6-(1-methylpyrrol-2-yl)-1,3,5-triazine, 2,4-bis{[4-tris(trimethylsiloxy-silylpropyloxy)-2-hydroxy]-phenyl}-6-(4-methoxyphenyl)-1,3,5-triazine, 2,4-bis{[4-(2"-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2"-methylpropyloxy)-2-hydroxy]phenyl}-6-(4-methoxy-phenyl)-1,3,5-triazine.

An advantageous broadspectrum filter within the scope of the present invention is 2,2'-methylenebis(6-(2H-benzotriazol-2-yl)-4-(1,1,3,3-tetramethylbutyl)phenol), which is available under the trade name Tinosorb® M from CIBA-Chemikalien GmbH.

An advantageous broadspectrum filter within the scope of the present invention is also 2-(2H-benzotriazol-2-yl)-4-methyl-6-[2-methyl-3-[1,3,3,3-tetramethyl-1-[(trimethylsilyl)oxy]disiloxanyl]propyl]phenol (CAS No.: 155633-54-8) with the INCI name Drometrizole Trisiloxane.

The UV-B and/or broadspectrum filters may be oil-soluble or water-soluble. Advantageous oil-soluble UV-B and/or broadspectrum filter substances are, e.g.:

- 3-benzylidenecamphor derivatives, preferably 3-(4-methylbenzylidene)camphor, 3-benzylidenecamphor;
- 4-aminobenzoic acid derivatives, preferably (2-ethylhexyl)4-(dimethylamino)benzoate, amyl 4-(dimethylamino)benzoate;
- 2,4,6-trianilino(p-carbo-2'-ethyl-1'-hexyloxy)-1,3,5-triazine;
- esters of benzalmalonic acid, preferably di(2-ethylhexyl) 4-methoxybenzalmalonate;
- esters of cinnamic acid, preferably (2-ethylhexyl) 4-methoxycinnamate, isopentyl 4-methoxycinnamate;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Advantageous water-soluble UV-B and/or broadspectrum filter substances are, e.g.:

- salts of 2-phenylbenzimidazole-5-sulfonic acid, such as its sodium, potassium or its triethanolammonium salt, and the sulfonic acid itself;
- sulfonic acid derivatives of 3-benzylidenecamphor, such as, e.g., 4-(2-oxo-3-bornylidenemethyl)benzenesulfonic acid, 2-methyl-5-(2-oxo-3-bornylidene methyl)-sulfonic acid and salts thereof.

A further light protection filter substance which can be used advantageously according to the invention is 2'-ethylhexyl 2-cyano-3,3-diphenylacrylic acid (octocrylene), which is available from BASF under the designation Uvinul® N 539.

It may also be considerably advantageous to use polymer-bound or polymeric UV filter substances in preparations according to the present invention, in particular those described in WO-A-92/20690.

In addition, it can optionally be advantageous to incorporate further UV-A and/or UV-B filters into cosmetic or dermatological preparations according to the invention, for example, certain salicylic acid derivatives, such as 4-isopropylbenzyl salicylate, 2-ethylhexyl salicylate (=Octyl salicylate), homomethyl salicylate.

The list of cited UV filters which can be used within the scope of the present invention is not of course intended to be limiting.

The following examples are intended to illustrate the present invention, without restricting it. Unless otherwise indicated, all amounts, proportions and percentages are relative to the weight and the total amount or the total weight of the preparations.

Examples O/W Creams

| Example No. | 1 | 2 | 3 | 4 | 5 | 6 |
|---|---|---|---|---|---|---|
| Glyceryl stearate citrate | | | 2.00 | 2.00 | | 2.00 |
| Glyceryl stearate self-emulsifying | 4.00 | 3.00 | | | | |
| PEG 40 stearate | 1.00 | | | | | |
| Polyglyceryl-3 Methylglucose Distearate | | | | | 3.00 | |
| Sorbitan stearate | | | | | | 2.00 |
| Stearic acid | | 1.00 | | | | |
| Stearyl alcohol | | | 2.00 | 2.00 | | |
| Cetyl alcohol | 3.00 | 2.00 | | | 3.00 | |
| Cetyl stearyl alcohol | | | | | | 2.00 |
| Lanolin alcohol | | | 1.00 | 1.00 | | |
| Caprylic/Capric triglyceride | 5.00 | 3.00 | 4.00 | 4.00 | 3.00 | 3.00 |
| Octyldodecanol | | | | | | 2.00 |
| Dicaprylyl ether | | 4.00 | | | 2.00 | 1.00 |
| Paraffinum liquidum | 5.00 | 2.00 | 8.00 | 8.00 | 3.00 | |
| Dimethicone | | | 1.00 | 1.00 | | |
| Aqua licorice extract P-U | 0.25 | 0.05 | 0.15 | 0.15 | 1.00 | 0.05 |
| Tocopherol | 0.1 | | | | | 0.20 |
| Na₃HEDTA | 0.1 | | | | 0.1 | |
| Preservatives | q.s | q.s | | | q.s. | q.s. |
| Polyacrylic acid | 3.00 | 0.1 | | | 0.1 | 0.1 |
| aqueous NaOH 45% | q.s | q.s | q.s | q.s | q.s | q.s |
| Glycerin | 5.00 | 3.00 | 7.50 | 7.50 | 3.00 | 3.00 |
| Butylene glycol | | 3.00 | | | | |
| Dihydroxyacetone | | | | 1.00 | | |
| Perfume | q.s | q.s | q.s | q.s | q.s | q.s |
| Water | ad 100 | ad 100 | ad 100 | ad 100 | ad 100 | ad 100 |

Examples O/W Creams

| Example No. | 7 | 8 | 9 | 10 | 11 |
|---|---|---|---|---|---|
| Glyceryl stearate citrate | | 2.00 | 2.00 | | |
| Glyceryl stearate self-emulsifying | 5.00 | | | | |
| Stearic acid | | | | 2.50 | 3.50 |
| Stearyl alcohol | 2.00 | | | | |
| Cetyl alcohol | | | | 3.00 | 4.50 |
| Cetyl stearyl alcohol | | 3.00 | 1.00 | | 0.50 |
| C₁₂₋₁₅ alkyl benzoate | | 2.00 | 3.00 | | |
| Caprylic/Capric triglyceride | 2.00 | | | | |
| Octyldodecanol | 2.00 | 2.00 | | 4.00 | 6.00 |

-continued

Examples W/O Creams (continued)

| Example No. | 7 | 8 | 9 | 10 | 11 |
|---|---|---|---|---|---|
| Paraffinum liquidum | | 4.00 | 2.00 | | |
| Cyclic dimethylpolysiloxane | | | | 0.50 | 2.00 |
| Dimethicone polydimethylsiloxane | 2.00 | | | | |
| Titanium dioxide | 2.00 | | | | |
| 4-methylbenzylidene camphor | 1.00 | | | | 1.00 |
| Butyl methoxydibenzoylmethane | 0.50 | | | | 0.50 |
| Aqua licorice extract P-U | 0.08 | 0.50 | 0.25 | 1.00 | 0.40 |
| 2,4-bis{[4-(2-ethyl-hexyloxy)-2-hydroxyl]phenyl}-6-(4-methoxyphenyl)-1,3,5-triazine | | 1.0 | 3.0 | | 0.5 |
| Dihydroxyacetone | | 0.5 | | | 0.5 |
| Tocopherol | | | | | 0.05 |
| Ethylene diamine tetraacetic acid trisodium | | | | 0.20 | 0.20 |
| Preservatives, perfume | q.s. | q.s. | q.s. | q.s. | q.s. |
| Xanthan gum | | | 0.20 | | |
| Polyacrylic acid | 0.15 | 0.1 | | 0.05 | 0.05 |
| aqueous NaOH 45% | q.s. | q.s. | q.s. | q.s. | q.s. |
| Glycerin | 3.00 | | 3.00 | 5.00 | 3.00 |
| Butylene glycol | | 3.00 | | | |
| Ethanol | | 3.00 | | 3.00 | |
| Water | ad 100 | ad 100 | ad 100 | ad 100 | ad 100 |

Examples W/O Creams

| Example No. | 12 | 13 | 14 | 15 | 16 |
|---|---|---|---|---|---|
| Cetyl dimethicone copolyol | | 2.50 | | 4.00 | |
| Polyglyceryl-2 Dipolyhydroxystearate | 5.00 | | | | 4.50 |
| PEG-30 Dipolyhydroxystearate | | | 5.00 | | |
| 2-ethylhexyl methoxycinnamate | | 8.00 | | 5.00 | 4.00 |
| 2,4-bis{[4-(2-ethyl-hexyloxy)-2-hydroxyl]phenyl}-6-(4-methoxyphenyl)-1,3,5-triazine | 2.00 | 2.50 | | 2.00 | 2.50 |
| Butylmethoxy dibenzoyl-methane | | | 2.00 | 1.00 | |
| Diethylhexyl Butamide Triazone | 3.00 | 1.00 | | | 3.00 |
| Ethylhexyl Triazone | | | 3.00 | 4.00 | |
| 4-Methylbenzylidene camphor | | 2.00 | | 4.00 | 2.00 |
| Octocrylene | 7.00 | 2.50 | 4.00 | | 2.50 |
| Diethylhexyl Butamide Triazone | 1.00 | | | 2.00 | |
| Phenylene-1,4-bis(monosodium,-2-benzimidazyl-5,7-disulfonic acid) | 1.00 | 2.00 | 0.50 | | |
| Phenylbenzimidazole sulfonic acid | 0.50 | | | 3.00 | 2.00 |
| Titanium dioxide | | 2.00 | 1.50 | | 3.00 |
| Zinc oxide | 3.00 | 1.00 | 2.00 | 0.50 | |
| Paraffinum liquidum | | | 10.0 | | 8.0 |
| C$_{12-15}$ alkyl benzoate | | | | 9.00 | |
| Dicaprylyl ether | 10.0 | | | | 7.00 |
| Butylene Glycol Dicaprylate/Dicaprate | | | 2.00 | 8.00 | 4.00 |
| Dicaprylyl carbonate | 5.00 | | 6.00 | | |
| Dimethicone polydimethylsiloxane | | 4.00 | 1.00 | 5.00 | |
| Phenylmethylpolysiloxane | 2.00 | 25.00 | | | 2.00 |
| Shea butter | | | 3.00 | | |
| PVP Hexadecene copolymer | 0.50 | | | 0.50 | 1.00 |
| Octoxyglycerin | | 0.30 | 1.00 | | 0.50 |
| Glycerin | 3.00 | 7.50 | | 7.50 | 2.50 |
| Glycine soja | | 1.00 | 1.50 | | |
| Magnesium sulfate | 1.00 | 0.50 | | 0.50 | |
| Magnesium chloride | | | 1.00 | | 0.70 |
| Tocopherol acetate | 0.50 | | 0.25 | | 1.00 |
| Aqua Licorice Extract P-U | 0.15 | 0.08 | 0.5 | 1.00 | 0.80 |
| Preservatives, perfume | q.s. | q.s. | q.s. | q.s. | q.s. |
| Ethanol | 3.00 | | 1.50 | | 1.00 |
| Water | ad 100 | ad 100 | ad 100 | ad 100 | ad 100 |

Examples W/O Emulsions

| | Example No. | |
|---|---|---|
| | 17 | 18 |
| Polyglyceryl-2 Dipolyhydroxystearate | 4.00 | 5.00 |
| Lanolin alcohol | 0.50 | 1.50 |
| Isohexadecane | 1.00 | 2.00 |
| Myristyl myristate | 0.50 | 1.50 |
| Vaseline | 1.00 | 2.00 |
| Butylmethoxy dibenzoylmethane | 0.50 | 1.50 |
| 4-Methylbenzylidene camphor | 1.00 | 3.00 |
| Butylene Glycol Dicaprylate/Dicaprate | 4.00 | 5.00 |
| Shea butter | — | 0.50 |
| Butylene glycol | — | 6.00 |
| Octoxyglycerin | — | 3.00 |
| Glycerin | 5.00 | — |
| Tocopherol acetate | 0.50 | 1.00 |
| Aqua Licorice Extract P-U | 0.2 | 0.1 |
| EDTA | 0.20 | 0.20 |
| Preservatives | q.s. | q.s. |
| Ethanol | — | 3.00 |
| Perfume | q.s. | q.s. |
| Water | ad 100 | ad 100 |

Example (W/O Cream)

| | Example No. 19 |
|---|---|
| Polyglyceryl-3-diisostearate | 3.50 |
| Glycerin | 3.00 |
| Polyglyceryl-2 Dipolyhydroxystearate | 3.50 |
| Aqua Licorice Extract P-U | 0.25 |
| Preservatives | q.s. |
| Perfume | q.s. |
| Magnesium sulfate | 0.6 |
| Isopropyl stearate | 2.0 |
| Caprylyl ether | 8.0 |
| Cetearyl isononanoate | 6.0 |
| Water | ad 100 |

Example (W/O Emulsion):

| | Example No. 20 |
|---|---|
| Triceteareth-4 phosphate | 0.80 |
| Butylated hydroxytoluene | 0.05 |
| Glyceryl Lanolate | 1.70 |
| Cyclomethicone | 2.20 |
| Isopropyl palmitate | 1.00 |
| Aqua Licorice Extract P-U | 0.50 |
| Polyacrylic acid | 0.50 |
| Ethylene diamine tetraacetic acid | 1.00 |
| Sodium hydroxide | q.s. |
| Citric acid | 0.01 |
| Preservatives | q.s. |
| Perfume | q.s. |
| Water | ad 100 |

What is claimed is:

1. A cosmetic or dermatological composition, wherein the composition comprises licochalcone A and at least one of an ethoxylated and a propoxylated raw material, and is associated with instructions to use the composition for at least one of the treatment and alleviation of erythema.

2. The composition of claim 1, wherein the composition comprises a plant extract which comprises licochalcone A.

3. The composition of claim 1, wherein the composition comprises an extract of Radix Glycyrrhicae inflatae which comprises licochalcone A.

4. A method of treating or alleviating erythema of skin, wherein the method comprises applying to skin in need thereof the cosmetic or dermatological composition of claim 1.

5. The composition of claim 1, wherein the composition comprises from 0.0001% to 5% by weight of licochalcone A.

6. The composition of claim 1, wherein the composition comprises from 0.001% to 1% by weight of licochalcone A.

7. The composition of claim 1, wherein the at least one of an ethoxylated and a propoxylated raw material comprises PPG-6-decyltetradeceth-30.

8. The composition of claim 1, wherein the composition is a W/O emulsion.

9. The composition of claim 1, wherein the composition is an O/W emulsion.

10. The composition of claim 1, wherein the composition is a W/O/W or O/W/O emulsion.

11. The composition of claim 1, wherein the composition further comprises at least one polyol.

12. The composition of claim 11, wherein the at least one polyol comprises butylene glycol.

13. The composition of claim 2, wherein the composition comprises from 0.001% to 1% by weight of licochalcone A.

14. The composition of claim 3, wherein the composition comprises from 0.001% to 1% by weight of licochalcone A.

15. The composition of claim 2, wherein the at least one of an ethoxylated and a propoxylated raw material comprises PPG-6-decyltetradeceth-30.

16. The composition of claim 2, wherein the composition is a W/O emulsion.

17. The composition of claim 2, wherein the composition is an O/W emulsion.

18. The composition of claim 2, wherein the composition further comprises at least one polyol.

19. The composition of claim 18, wherein the at least one polyol comprises butylene glycol.

20. The composition of claim 3, wherein the composition further comprises at least one polyol.

* * * * *